US006783761B2

(12) United States Patent
Grimes et al.

(10) Patent No.: US 6,783,761 B2
(45) Date of Patent: Aug. 31, 2004

(54) CHIMERIC PEPTIDE IMMUNOGENS

(75) Inventors: Stephen Grimes, Davis, CA (US); Dov Michaeli, Larkspur, CA (US); Vernon C. Stevens, Dublin, OH (US)

(73) Assignee: Aphton Corporation, Woodland, CA (US)

( * ) Notice: Subject to any disclaimer, the term of this patent is extended or adjusted under 35 U.S.C. 154(b) by 0 days.

(21) Appl. No.: 09/848,834

(22) Filed: May 4, 2001

(65) Prior Publication Data

US 2002/0076416 A1 Jun. 20, 2002

Related U.S. Application Data

(60) Provisional application No. 60/202,328, filed on May 5, 2000.

(51) Int. Cl.[7] ........................ A61K 39/00; A61K 38/16; A61K 38/24
(52) U.S. Cl. ................................ 424/185.1; 424/192.1; 530/324; 530/328; 530/313
(58) Field of Search .................................. 530/324, 328, 530/313, 330; 424/185.1, 192.1

(56) References Cited

U.S. PATENT DOCUMENTS

| | | |
|---|---|---|
| 4,201,770 A | 5/1980 | Stevens |
| 4,302,386 A | 11/1981 | Stevens |
| 4,384,995 A | 5/1983 | Stevens |
| 4,526,716 A | 7/1985 | Stevens |
| 4,608,251 A | 8/1986 | Mia |
| 4,618,598 A | 10/1986 | Conn |
| 4,691,006 A | 9/1987 | Stevens |
| 4,780,312 A | 10/1988 | Talwar |
| 5,023,077 A | 6/1991 | Gevas et al. |
| 5,036,047 A | 7/1991 | Mia |
| 5,109,026 A | 4/1992 | Hoskinson |
| 5,204,108 A | 4/1993 | Illum |
| 5,324,512 A | 6/1994 | Ladd et al. |
| 5,378,688 A | 1/1995 | Nett et al. |
| 5,403,586 A | 4/1995 | Russell-Jones et al. |
| 5,422,110 A | 6/1995 | Potter et al. |
| 5,468,494 A | 11/1995 | Gevas et al. |
| 5,484,592 A | 1/1996 | Meloen et al. |
| 5,488,036 A | 1/1996 | Nett et al. |
| 5,633,248 A | 5/1997 | Kato et al. |
| 5,648,340 A | 7/1997 | Barnea |
| 5,684,145 A | 11/1997 | Vander Zee |
| 5,688,506 A | 11/1997 | Grimes et al. |
| 5,708,155 A | 1/1998 | Potter et al. |
| 5,723,129 A | 3/1998 | Potter et al. |
| 5,759,551 A | 6/1998 | Ladd et al. |
| 5,817,753 A | 10/1998 | Stevens |
| 5,837,268 A | 11/1998 | Potter et al. |
| 5,843,446 A | 12/1998 | Ladd et al. |
| 5,885,966 A | 3/1999 | Meloen et al. |
| 6,025,468 A | 2/2000 | Wang |
| 6,228,987 B1 | 5/2001 | Wang |

FOREIGN PATENT DOCUMENTS

| | | |
|---|---|---|
| EP | 0578293 | 1/1994 |
| GB | 2228262 | 1/1990 |
| WO | 9002187 | 3/1990 |
| WO | 9102799 | 3/1991 |
| WO | 9219746 | 11/1992 |
| WO | 9425060 | 11/1994 |
| WO | 9715325 | 5/1997 |
| WO | 9966952 | 12/1999 |

OTHER PUBLICATIONS

Kaumaya, Pravin T.P., Susan Kobs–Conrad, Ann M. DiGeorge, and Vernon C. Stevens, "De Novo Engineering of Peptide Immunogenic and Antigenic Determinants as Potential Vaccines" in *Peptide: Design, Synthesis, and Biological Activity* pp. 133–164. Channa Basava and G.M. Ananthatamaiah (Eds.) Birkhauser, Boston 1994.

Young Hoon Seo, Susan Kobs–Conrad and Pravin T.P. Kaumaya. "Promiscuous T–Cell Epitopes of Tetanus Toxoid and Measles Virus Enhance Immune Responses to B–Cell Epitopes of the Prokin antigen LDH–$C_4$," in *Peptides* pp. 866–867. 1992 C.H. Schneider and A.N. Eberle (Eds.) 1993 ESCOM Science Publishe BV.

Pravin T.P.Kaumaya, Susan Kobs–Conrad, Young Hoon–Seo and Ann Marie DiGeorge "Template Vaccine Strategy Bypasses Hapto Type– Restricted Immune Responses" in *Peptide 1992* pp. 139–141. C.H. Schneider and A.N. Eberle (Eds.) 1993 *ESCOM* Science Publisher BV.

Susan F. Kobs–Conrad, Ann Marie DiGeorge, Hyosil Lee and Pravin T.P. Kaumaya "Folding and Immunogenicity of a Loop–Structured Peptide Using the Zinc–Finger Motif" in *Peptides* 1992 C.H. Schneider And A.N. Eberle (Eds.) 1993 *ESCOM Science* Publisher BV.

Pravin T.P. Kaumaya, Susan Kobs–Conrad, Young Hoon–Lee, Hyosil Lee, Anne M. Van Buskirk, Ningguo Feug, John F. Sheridan and Vernon Stevens "Peptide Vaccines Incorporating a 'Promiscuous' T–Cell Epitope Bypass Certain Haplotype Restricted Immune Responses and Provide Broad Spectrum Immunogenicity". *Journal of Molecular Recognition*, vol. 6, 81–91 (1993).

(List continued on next page.)

Primary Examiner—Christina Chan
Assistant Examiner—Phuong Huynh
(74) Attorney, Agent, or Firm—White & Case LLP

(57) ABSTRACT

Chimeric peptide epitopes can serve as effective immunogens against hormones and other small peptides or proteins. Thus, immunogenic peptides are selected from promiscuous Th epitopes and synthesized together with self antigenic peptide sequences fused with or without end to end spacer peptide interconnections. A peptide sequence which may be of the gonadotropin releasing hormone is linked with an immunogenic peptide sequence selected from a promiscuous Th-epitope of measles virus protein F, tetanus toxoid, or malaria protein CSP. Compositions of the chimeric immunogen are found effective in eliciting high and specific anti-GnRH antibody titers.

14 Claims, 2 Drawing Sheets

OTHER PUBLICATIONS

Figure 1:
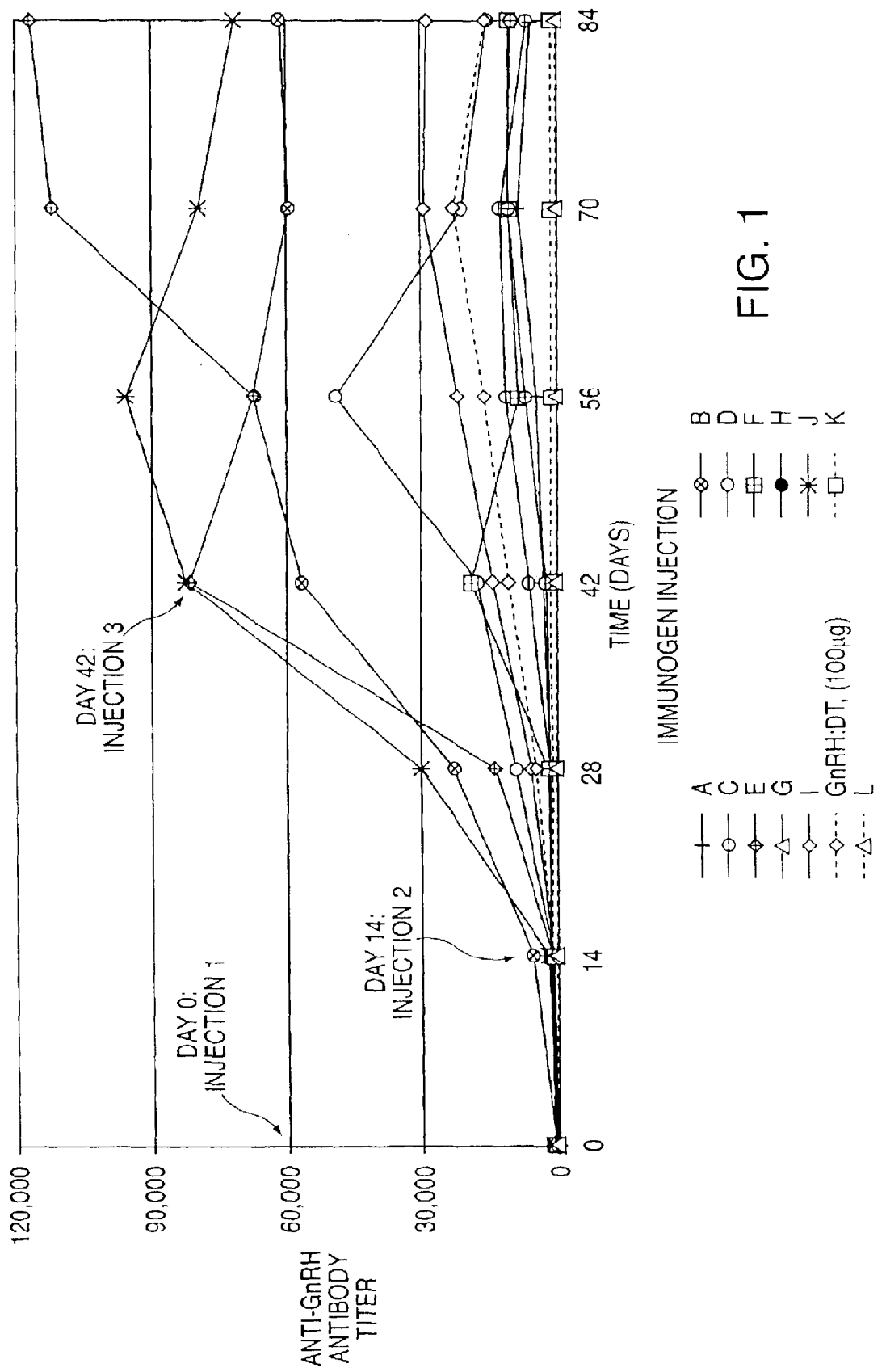

Susan Kobs–Conrad, Hyosil Lee, Ann M. DiGeorge, and Pravin T.P. Kaumaya "Engineered Topographic Determinants with $\alpha\beta$, $\beta\&\beta$, and $\beta\alpha\beta\alpha$ Topologies Show High Affinity Binding to Native Protein Antigen (Lactate dehydrogenase–$C_4$)" (1993) *The Journal of Biological Chemistry* 268(34): 25285–25295.

Pravin T.P. Kaumaya, Anne M. Vau Buskirk, Eruin Goldberg, and Susan U. Piece "Design and Immunological Properties of Topographic Immunogenic Determinants of a Protein Antigen (LDH–$C_4$) as Vaccines".(1992) *Journal of Biological Chemistry* 267(9): 6338–6346.

Susan F. Conrad, In–Ja L. Byeon, Ann M. DiGeorge, Michael D. Lairmore, Ming–Daw Tsai and Pravin T.P. Kaumay. Immunogenicity and Conformational Properties of an N–Linked Glycosylated Peptide Epitope of Human T–Lymophotropic Virus Type 1 (HTLV–I)– *Biomedical Peptides, Proteins & Nucleic Acids*, vol. 1, 83–92 (1995).

Pierre L. Triozzi, Gary D. Stoner and Pravin T.P. Kaumaya "Subunit Peptide Cancer Vaccines Targeting Activating Mutations of the p21 Ras Proto–Oncogene". *Biomedical Peptides, Proteins & Nucleic Acids*, vol. 1, 185–192 (1995).

Michael D. Lairmore, Renu B. Lal, and Pravin T.P. Kaumaya. Evaluation of Immunodominant Epitopes of Human T–Lymphotropic Virus Type 1 (HTLV–I) Using Synthetic Peptides. *Biomedical Peptides, Proteins & Nucleic Acids*, vol. 1, 117–122 (1995).

Michael D. Lairmore, Ann M. DiGeorge, Susan F. Conrad, Ales V. Trevino, Renu B. Lal, and Pravin T.P. Kaumaya. "Human T–lymphotropic virus type 1 peptides in chimeric and multivalent constructs with promiscuous T–Cell epitopes enhance immunogenicity and overcome genetic restriction", *Journal of Virology*. Oct. 1995, pp. 6077–6089.

Thomas P. Hopp and Kenneth R. Woods. "Prediction of Protein Antigenic Determinants from Amino Acid Sequences". *Proc. Natl. Acad. Sci. USA* 78 (1981).

Gjalt W. Welling, Wicher J. Weijer, Ruurd van der Zee and Sytske Welling Wester. "Prediction of Sequential Antigenic Regions in Proteins". *FEBS* vol. 188(2), p. 215–219; Sep. 1985.

Jack Kyte and Russell F. Doolittle. "A Simple method for displaying the hydropathic character of a protein". *J. Mol. Biol.* (1982) 157, 105–132.

J.M. Thornton, M.S. Edwards, W.R. Taylor and D.J. Barlow. "Location of 'Continuous' Antigenic determinants in the protruding regions of proteins" (1986); pp. 409–411.

P.A. Karplus and G.E. Schulz. "Prediction of chain flexibility in proteins". *Naturwissenschaften* 72(1985) 212–213.

George D. Rose, Ari R. Geselowitz, Glenn J. Lesser, Richard H. Lee, Michael H. Zchfus. "Hydrophobicity of amino acid residues in globular proteins". Science 229: 834–838.

Peter Y. Chou and Gerald D. Fasman. "Prediction of the secondary structure of proteins from their amino acid Sequence" pp. 45–141.

Pravin T.P. Kaumaya. "Synthetic Peptide Vaccines: Dream or Reality?" *Peptides in Immunology*. C.H. Schneider, Ed. 1996. John Wiley & Sons, Ltd. p. 117–148.

Pravin T.P. Kaumaya, Susan Kobs–Conrd, and Ann M. DiGeorge. "Synthetic Peptide Vaccines: Misconceptions and Problems, Strategies and Prospects". Chapter 42 in pp. 279–292.

Lori A. Smolenski, Pravin Kaumaya, M. Zouhair Atassi and Susan K. Pierce. "Characteristics of Peptides Which Compete for Presented Antigen–Binding Sites on Antigen–Presenting Cells". *Eur. J. Immunol.* 1990. 20: 953–960.

Lisa A. Casten, Pravin Kaumaya, and Susan K. Pierce. "Enhanced T–Cell Responses to Antigenic Peptides Targeted to B–Cell Surface Ig, In, or Class I Molecules". *J. Exp. Med.* vol. 168 (1988), 171–180.

A. Ladd Review: Progress in the development of anti–L-HRH vaccine. American J. Reproductive Immunology 29 (1993) 189–194.

S. Sad et al. "Synthetic gonadotrophin–releasing hormone (GnRH) vaccines incorporating GnRH and synthetic T–helper epitopes." 1993 *Vaccine* 11: 1145–1147.

S. Ghosh and D.C. Jackson "Antigenic and immunogenic properties of totally synthetic peptide–based anti–fertility vaccines" (1999) *International Immunology* 11 (7) pp. 1103–1110.

S. Sad, K. Rao et al. "Bypass of carrier–induced epitope-specific suppression using a T–helper epitope", Immunology.

SEQUENCE LISTING

<160> NUMBER OF SEQ ID NOS: 20

<210> SEQ ID NO 1
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Pyroglutamic acid or 5-oxoproline
<221> NAME/KEY: MOD_RES
<222> LOCATION: (10)..(10)
<223> OTHER INFORMATION: Amidated-glycine or glycinamide

<400> SEQUENCE: 1

Xaa His Trp Ser Tyr Gly Leu Arg Pro Xaa
1               5                   10

<210> SEQ ID NO 2
<211> LENGTH: 16
<212> TYPE: PRT
<213> ORGANISM: Tetanus bacillus
<220> FEATURE:
<221> NAME/KEY: PEPTIDE
<222> LOCATION: (1)..(16)
<223> OTHER INFORMATION: Amino acid sequence 829-844 of the Tetanus
      Toxoid Precursor (Tentoxylysin)

<400> SEQUENCE: 2

Met Gln Tyr Ile Lys Ala Asn Ser Lys Phe Ile Gly Ile Thr Glu Leu

```
<210> SEQ ID NO 3
<211> LENGTH: 20
<212> TYPE: PRT
<213> ORGANISM: Plasmodium falciparum
<220> FEATURE:
<221> NAME/KEY: PEPTIDE
<222> LOCATION: (1)..(20)
<223> OTHER INFORMATION: Amino acid sequence 378-398 of the Plamodium
      falciparum circumsporozoite (CSP) protein

<400> SEQUENCE: 3

Asp Glu Lys Lys Ile Ala Lys Met Glu Lys Ala Ser Ser Val Phe Asn
1               5                   10                  15

Val Val Asn Ser
            20

<210> SEQ ID NO 4
<211> LENGTH: 21
<212> TYPE: PRT
<213> ORGANISM: Tetanus bacillus
<220> FEATURE:
<221> NAME/KEY: PEPTIDE
<222> LOCATION: (1)..(21)
<223> OTHER INFORMATION: Amino acid sequence 947-967 of Tetanus
      Toxoid Precursor (Tentoxylysin)

<400> SEQUENCE: 4

Phe Asn Asn Phe Thr Val Ser Phe Trp Leu Arg Val Pro Lys Val Ser
1               5                   10                  15

Ala Ser His Leu Glu
            20

<210> SEQ ID NO 5
<211> LENGTH: 4
<212> TYPE: PRT
<213> ORGANISM: Artificial Sequence
<220> FEATURE:
<223> OTHER INFORMATION: Synthetic peptide

<400> SEQUENCE: 5

Gly Pro Ser Leu
1

<210> SEQ ID NO 6
<211> LENGTH: 6
<212> TYPE: PRT
<213> ORGANISM: Artificial Sequence
<220> FEATURE:
<223> OTHER INFORMATION: Synthetic peptide

<400> SEQUENCE: 6

Ser Ser Gly Pro Ser Leu
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic peptide

<400> SEQUENCE: 7

Ser Ser Gly Pro Ser Leu Lys Leu
1               5
```

```
<210> SEQ ID NO 8
<211> LENGTH: 16
<212> TYPE: PRT
<213> ORGANISM: Measles virus
<220> FEATURE:
<221> NAME/KEY: PEPTIDE
<222> LOCATION: (1)..(16)
<223> OTHER INFORMATION: Amino acid sequence 288-302 of the measles
      virus fusion protein, F

<400> SEQUENCE: 8

Leu Ser Glu Ile Lys Gly Val Ile Val His Arg Leu Glu Gly Val Glu
1               5                   10                  15

<210> SEQ ID NO 9
<211> LENGTH: 31
<212> TYPE: PRT
<213> ORGANISM: Artificial Sequence
<220> FEATURE:
<223> OTHER INFORMATION: Chimeric peptide made up of amino acid sequence
      288-302 of the Me asels virus fusion protein, F linked by a spacer
      peptide to amino acid sequence 2-10 of the GnRH hormone
<221> NAME/KEY: MOD_RES
<222> LOCATION: (1)..(1)
<223> OTHER INFORMATION: Amidated Lysine
<221> NAME/KEY: PEPTIDE
<222> LOCATION: (1)..(15)
<223> OTHER INFORMATION: Peptide corresponds to the amino acid sequences
      288-302 of the measles virus fusion protein, F
<221> NAME/KEY: PEPTIDE
<222> LOCATION: (19)..(22)
<223> OTHER INFORMATION: Spacer peptide
<221> NAME/KEY: PEPTIDE
<222> LOCATION: (23)..(31)
<223> OTHER INFORMATION: Peptide corresponds to amino acid sequences
      2-10 of the human GnRH hormone
<221> NAME/KEY: MOD_RES
<222> LOCATION: (31)..(31)
<223> OTHER INFORMATION: Amidated glycine or glycinamide

<400> SEQUENCE: 9

Lys Leu Leu Ser Glu Ile Lys Gly Val Ile Val His Arg Leu Glu Gly
1               5                   10                  15

Val Glu Gly Pro Ser Leu His Trp Ser Tyr Gly Leu Arg Pro Xaa
            20                  25                  30

<210> SEQ ID NO 10
<211> LENGTH: 34
<212> TYPE: PRT
<213> ORGANISM: Artificial Sequence
<220> FEATURE:
<223> OTHER INFORMATION: Chimeric peptide consisting of amino acid
      sequence 947-967 of the Tetanus toxoid precursor (Tentoxylysin)
      linked by a spacer to amino acid sequence 2-10 of the GnRH hormone
<221> NAME/KEY: MOD_RES
<222> LOCATION: (1)..(1)
<223> OTHER INFORMATION: Amidated phenylalanine
<221> NAME/KEY: PEPTIDE
<222> LOCATION: (1)..(21)
<223> OTHER INFORMATION: Amino acids 947-967 of the Tetanus Toxoid
      Precursor (Tentoxylysin)
<221> NAME/KEY: PEPTIDE
<222> LOCATION: (22)..(25)
<223> OTHER INFORMATION: Spacer peptide
<221> NAME/KEY: PEPTIDE
<222> LOCATION: (26)..(34)
<223> OTHER INFORMATION: Amino acids 2-10 of the human GnRH hormone
<221> NAME/KEY: MOD_RES
<222> LOCATION: (34)..(34)
<223> OTHER INFORMATION: Amidated glycine or glycinamide

<400> SEQUENCE: 10
```

```
Phe Asn Asn Phe Thr Val Ser Phe Trp Leu Arg Val Pro Lys Val Ser
1               5                   10                  15

Ala Ser His Leu Glu Gly Pro Ser Leu His Trp Ser Tyr Gly Leu Arg
            20                  25                  30

Pro Xaa
```

<210> SEQ ID NO 11
<211> LENGTH: 28
<212> TYPE: PRT
<213> ORGANISM: Artificial Sequence
<220> FEATURE:
<223> OTHER INFORMATION: Chimeric peptide consisting of amino acid
      sequence 830-844 of the Tetanus toxoid precursor (Tentoxylysin)
      linked by a spacer to amino acid sequence 2-10 of the GnRH hormone
<221> NAME/KEY: MOD_RES
<222> LOCATION: (1)..(1)
<223> OTHER INFORMATION: Amidated-glutamine
<221> NAME/KEY: MOD_RES
<222> LOCATION: (28)..(28)
<223> OTHER INFORMATION: Amidated-glycine or glycinamide
<221> NAME/KEY: PEPTIDE
<222> LOCATION: (1)..(15)
<223> OTHER INFORMATION: Amino acid sequence 830-844 of the Tetanus
      Toxoid Precursor (Tentoxylysin)
<221> NAME/KEY: PEPTIDE
<222> LOCATION: (16)..(19)
<223> OTHER INFORMATION: Spacer peptide
<221> NAME/KEY: PEPTIDE
<222> LOCATION: (20)..(28)
<223> OTHER INFORMATION: Amino acid sequence 2-10 of the human GnRH
      hormone

<400> SEQUENCE: 11

```
Gln Tyr Ile Lys Ala Asn Ser Lys Phe Ile Gly Ile Thr Glu Leu Gly
1               5                   10                  15

Pro Ser Leu His Trp Ser Tyr Gly Leu Arg Pro Xaa
            20                  25
```

<210> SEQ ID NO 12
<211> LENGTH: 33
<212> TYPE: PRT
<213> ORGANISM: Artificial Sequence
<220> FEATURE:
<223> OTHER INFORMATION: Chimeric peptide consisting of amino acid
      sequence 378-398 of the Plasmodium falciparum CSP protein linked
      by a spacer to amino acid sequence 2-10 of the GnRH hormone
<221> NAME/KEY: MOD_RES
<222> LOCATION: (1)..(1)
<223> OTHER INFORMATION: Amidated aspartic acid
<221> NAME/KEY: MOD_RES
<222> LOCATION: (33)..(33)
<223> OTHER INFORMATION: Amidated glycine or glycinamide
<221> NAME/KEY: PEPTIDE
<222> LOCATION: (1)..(20)
<223> OTHER INFORMATION: Amino acid sequence 378-398 of the Malaria
      (Plasmodium falciparum) circumsporozoite
      ( CSP) protein
<221> NAME/KEY: PEPTIDE
<222> LOCATION: (21)..(24)
<223> OTHER INFORMATION: Spacer peptide
<221> NAME/KEY: PEPTIDE
<222> LOCATION: (25)..(33)
<223> OTHER INFORMATION: Amino acid sequence 2-10 of the human GnRH
      hormone

<400> SEQUENCE: 12

```
Asp Glu Lys Lys Ile Ala Lys Met Glu Lys Ala Ser Ser Val Phe Asn
1               5                   10                  15

Val Val Asn Ser Gly Pro Ser Leu His Trp Ser Tyr Gly Leu Arg Pro
            20                  25                  30
```

-continued

Xaa

```
<210> SEQ ID NO 13
<211> LENGTH: 34
<212> TYPE: PRT
<213> ORGANISM: Artificial Sequence
<220> FEATURE:
<223> OTHER INFORMATION: Chimeric peptide consisting of amino acid
      sequence 1-10 of the GnRH hormone linked by a spacer to amino acid
      sequence 288-302 of the Measles virus fusion protein,
<221> NAME/KEY: PEPTIDE
<222> LOCATION: (1)..(10)
<223> OTHER INFORMATION: Amino acid sequence 1-10 of the human GnRH
      hormone
<221> NAME/KEY: PEPTIDE
<222> LOCATION: (11)..(18)
<223> OTHER INFORMATION: Spacer peptide
<221> NAME/KEY: PEPTIDE
<222> LOCATION: (19)..(34)
<223> OTHER INFORMATION: Amino acid sequence 288-302 of the Measles
      virus fusion protein, F
<221> NAME/KEY: MOD_RES
<222> LOCATION: (1)..(1)
<223> OTHER INFORMATION: Pyroglutamic acid or 5-oxoproline

<400> SEQUENCE: 13

Xaa His Trp Ser Tyr Gly Leu Arg Pro Gly Ser Ser Gly Pro Ser Leu
1               5                   10                  15

Lys Leu Leu Ser Glu Ile Lys Gly Val Ile Val His Arg Leu Glu Gly
            20                  25                  30

Val Glu

<210> SEQ ID NO 14
<211> LENGTH: 37
<212> TYPE: PRT
<213> ORGANISM: Artificial Sequence
<220> FEATURE:
<223> OTHER INFORMATION: Chimeric peptide consisting of amino acid
      sequence 1-10 of the GnRH hormone linked by a spacer to amino acid
      sequence 947-967 of the Tetanus toxoid precursor (Tentoxylysin)
<221> NAME/KEY: MOD_RES
<222> LOCATION: (1)..(1)
<223> OTHER INFORMATION: Pyroglutamic acid or 5-oxoproline
<221> NAME/KEY: PEPTIDE
<222> LOCATION: (1)..(10)
<223> OTHER INFORMATION: Amino acid sequence 1-10 of the human GnRH
      hormone
<221> NAME/KEY: PEPTIDE
<222> LOCATION: (11)..(16)
<223> OTHER INFORMATION: Spacer peptide
<221> NAME/KEY: PEPTIDE
<222> LOCATION: (17)..(37)
<223> OTHER INFORMATION: Amino acid sequence 947-967 of the Tetanus
      toxoid precursor (Tentoxylysin)

<400> SEQUENCE: 14

Xaa His Trp Ser Tyr Gly Leu Arg Pro Gly Ser Ser Gly Pro Ser Leu
1               5                   10                  15

Phe Asn Asn Phe Thr Val Ser Phe Trp Leu Arg Val Pro Lys Val Ser
            20                  25                  30

Ala Ser His Leu Glu
        35

<210> SEQ ID NO 15
<211> LENGTH: 31
<212> TYPE: PRT
<213> ORGANISM: Artificial Sequence
<220> FEATURE:
<223> OTHER INFORMATION: Chimeric peptide consisting of amino acid
      sequence 1-10 of the GnRH hormone linked by a spacer to amino
```

-continued

```
      sequence 830-844 of the Tetanus toxoid precursor (Tentoxylysin)
<221> NAME/KEY: MOD_RES
<222> LOCATION: (1)..(1)
<223> OTHER INFORMATION: Pyroglutamic acid or 5-oxoproline
<221> NAME/KEY: PEPTIDE
<222> LOCATION: (1)..(10)
<223> OTHER INFORMATION: Amino acid sequence 1-10 of the human GnRH
      hormone
<221> NAME/KEY: PEPTIDE
<222> LOCATION: (11)..(16)
<223> OTHER INFORMATION: Spacer peptide
<221> NAME/KEY: PEPTIDE
<222> LOCATION: (17)..(31)
<223> OTHER INFORMATION: Amino acid sequence 830-844 of the Tetanus
      toxoid precursor (Tentoxylysin)

<400> SEQUENCE: 15

Xaa His Trp Ser Tyr Gly Leu Arg Pro Gly Ser Ser Gly Pro Ser Leu
 1               5                  10                  15

Gln Tyr Ile Lys Ala Asn Ser Lys Phe Ile Gly Ile Thr Glu Leu
             20                  25                  30

<210> SEQ ID NO 16
<211> LENGTH: 36
<212> TYPE: PRT
<213> ORGANISM: Artificial Sequence
<220> FEATURE:
<223> OTHER INFORMATION: Chimeric peptide consisting of amino acid
      sequence 1-10 of the GnRH hormone linked by a spacer to amino acid
      sequence 378-398 of the Plasmodium falciparum circumsporozoite
      (CSP) protein
<221> NAME/KEY: MOD_RES
<222> LOCATION: (1)..(1)
<223> OTHER INFORMATION: Pyroglutamic acid or 5-oxoproline
<221> NAME/KEY: PEPTIDE
<222> LOCATION: (1)..(10)
<223> OTHER INFORMATION: Amino acid sequence 1-10 of the human GnRH
      hormone
<221> NAME/KEY: PEPTIDE
<222> LOCATION: (11)..(16)
<223> OTHER INFORMATION: Spacer peptide
<221> NAME/KEY: PEPTIDE
<222> LOCATION: (17)..(36)
<223> OTHER INFORMATION: Amino acid sequence 378-398 of the Malaria
      (Plasmodium falciparum) circumsporozoite (CSP) protein

<400> SEQUENCE: 16

Xaa His Trp Ser Tyr Gly Leu Arg Pro Gly Ser Ser Gly Pro Ser Leu
 1               5                  10                  15

Asp Glu Lys Lys Ile Ala Lys Met Glu Lys Ala Ser Ser Val Phe Asn
             20                  25                  30

Val Val Asn Ser
         35

<210> SEQ ID NO 17
<211> LENGTH: 47
<212> TYPE: PRT
<213> ORGANISM: Artificial Sequence
<220> FEATURE:
<223> OTHER INFORMATION: Chimeric peptide consisting of amino acid
      sequence 1-10 of the GnRH hormone linked by a spacer to amino acid
      sequence 288-302 of the Measles virus protein F linked by a spacer
      to amino acid sequence 2-10 of the GnRH hormone
<221> NAME/KEY: MOD_RES
<222> LOCATION: (1)..(1)
<223> OTHER INFORMATION: Pyroglutamic acid or 5-oxoproline
<221> NAME/KEY: MOD_RES
<222> LOCATION: (47)..(47)
<223> OTHER INFORMATION: Amidated-glycine or glycinamide
<221> NAME/KEY: PEPTIDE
<222> LOCATION: (1)..(10)
<223> OTHER INFORMATION: Amino acid sequence 1-10 of the human GnRH
```

```
      hormone
<221> NAME/KEY: PEPTIDE
<222> LOCATION: (11)..(18)
<223> OTHER INFORMATION: Spacer peptide
<221> NAME/KEY: PEPTIDE
<222> LOCATION: (19)..(34)
<223> OTHER INFORMATION: Amino acid sequence 288-302 of the Measles
      virus fusion protein,
<221> NAME/KEY: PEPTIDE
<222> LOCATION: (35)..(38)
<223> OTHER INFORMATION: Spacer peptide
<221> NAME/KEY: PEPTIDE
<222> LOCATION: (39)..(47)
<223> OTHER INFORMATION: Amino acid sequence 2-10 of the human GnRH
      hormone

<400> SEQUENCE: 17

Xaa His Trp Ser Tyr Gly Leu Arg Pro Gly Ser Ser Gly Pro Ser Leu
1               5                   10                  15

Lys Leu Leu Ser Glu Ile Lys Gly Val Ile Val His Arg Leu Glu Gly
                20                  25                  30

Val Glu Gly Pro Ser Leu His Trp Ser Tyr Gly Leu Arg Pro Xaa
            35                  40                  45

<210> SEQ ID NO 18
<211> LENGTH: 50
<212> TYPE: PRT
<213> ORGANISM: Artificial Sequence
<220> FEATURE:
<223> OTHER INFORMATION: Chimeric peptide consisting of amino acid
      sequence 1-10 of human GnRH linked by a spacer to amino acid
      sequence 947-967 of the Tetanus toxoid precursor (Tentoxylysin)
      protein linked by a spacer to amino acid sequence 2-10 of human
      GnRH
<221> NAME/KEY: MOD_RES
<222> LOCATION: (1)..(1)
<223> OTHER INFORMATION: Pyroglutamic acid or 5-oxoproline
<221> NAME/KEY: MOD_RES
<222> LOCATION: (50)..(50)
<223> OTHER INFORMATION: Amidated glycine or glycinamide
<221> NAME/KEY: PEPTIDE
<222> LOCATION: (1)..(10)
<223> OTHER INFORMATION: Amino acid sequence 1-10 of the human GnRH
      hormone
<221> NAME/KEY: PEPTIDE
<222> LOCATION: (11)..(16)
<223> OTHER INFORMATION: Spacer peptide
<221> NAME/KEY: PEPTIDE
<222> LOCATION: (17)..(37)
<223> OTHER INFORMATION: Amino acid sequence 947-967 of the Tetanus
      toxoid precursor (Tentoxylysin)
<221> NAME/KEY: PEPTIDE
<222> LOCATION: (38)..(41)
<223> OTHER INFORMATION: Spacer peptide
<221> NAME/KEY: PEPTIDE
<222> LOCATION: (42)..(50)
<223> OTHER INFORMATION: Amino acid sequence 2-10 of the human GnRH
      hormone

<400> SEQUENCE: 18

Xaa His Trp Ser Tyr Gly Leu Arg Pro Gly Ser Ser Gly Pro Ser Leu
1               5                   10                  15

Phe Asn Asn Phe Thr Val Ser Phe Trp Leu Arg Val Pro Lys Val Ser
                20                  25                  30

Ala Ser His Leu Glu Gly Pro Ser Leu His Trp Ser Tyr Gly Leu Arg
            35                  40                  45

Pro Xaa
    50

<210> SEQ ID NO 19
```

```
<211> LENGTH: 46
<212> TYPE: PRT
<213> ORGANISM: Artificial Sequence
<220> FEATURE:
<223> OTHER INFORMATION: Chimeric peptide consisting of amino acid
      sequence 1-10 of human GnRH linked by a spacer to amino acid
      sequence 830-844 of Tetanus toxoid precursor (Tentoxylysin) linked
      by a spacer to amino acid sequence 1-10 of GnRH
<221> NAME/KEY: MOD_RES
<222> LOCATION: (1)..(1)
<223> OTHER INFORMATION: Pyroglutamic acid or 5-oxoproline
<221> NAME/KEY: MOD_RES
<222> LOCATION: (46)..(46)
<223> OTHER INFORMATION: Amidated glycine or glycinamide
<221> NAME/KEY: PEPTIDE
<222> LOCATION: (1)..(10)
<223> OTHER INFORMATION: Amino acid sequence 1-10 of the human GnRH
      hormone
<221> NAME/KEY: PEPTIDE
<222> LOCATION: (11)..(16)
<223> OTHER INFORMATION: Spacer peptide
<221> NAME/KEY: PEPTIDE
<222> LOCATION: (17)..(31)
<223> OTHER INFORMATION: Amino acid sequence 830-844 of the Tetanus
      toxoid precursor (Tentoxylysin)
<221> NAME/KEY: PEPTIDE
<222> LOCATION: (32)..(37)
<223> OTHER INFORMATION: Spacer peptide
<221> NAME/KEY: PEPTIDE
<222> LOCATION: (38)..(46)
<223> OTHER INFORMATION: Amino acid sequence 2-10 of the human GnRH
      hormone

<400> SEQUENCE: 19

Xaa His Trp Ser Tyr Gly Leu Arg Pro Gly Ser Ser Gly Pro Ser Leu
1               5                   10                  15

Gln Tyr Ile Lys Ala Asn Ser Lys Phe Ile Gly Ile Thr Glu Leu Ser
            20                  25                  30

Ser Gly Pro Ser Leu His Trp Ser Tyr Gly Leu Arg Pro Xaa
        35                  40                  45

<210> SEQ ID NO 20
<211> LENGTH: 51
<212> TYPE: PRT
<213> ORGANISM: Artificial Sequence
<220> FEATURE:
<223> OTHER INFORMATION: Chimeric peptide consisting of amino acid
      sequence 1-10 of human GnRH linked by a spacer to amino acid
      sequence 378-398 of Plasmodium falciparum circumsporozoite (CSP)
      protein
<221> NAME/KEY: MOD_RES
<222> LOCATION: (1)..(1)
<223> OTHER INFORMATION: Pyroglutamic acid or 5-oxoproline
<221> NAME/KEY: MOD_RES
<222> LOCATION: (51)..(51)
<223> OTHER INFORMATION: Amidated glycine or glycinamide
<221> NAME/KEY: PEPTIDE
<222> LOCATION: (1)..(10)
<223> OTHER INFORMATION: Amino acid sequence 1-10 of the human GnRH
      hormone
<221> NAME/KEY: PEPTIDE
<222> LOCATION: (11)..(16)
<223> OTHER INFORMATION: Spacer peptide
<221> NAME/KEY: PEPTIDE
<222> LOCATION: (17)..(36)
<223> OTHER INFORMATION: Amino acid sequence 378-398 of the Plasmodium
      falciparum circumsporozoite (CSP) protein
<221> NAME/KEY: PEPTIDE
<222> LOCATION: (37)..(42)
<223> OTHER INFORMATION: Spacer peptide
<221> NAME/KEY: PEPTIDE
<222> LOCATION: (43)..(51)
<223> OTHER INFORMATION: Amino acid sequence 2-10 of the human GnRH
      hormone
```

-continued

```
<400> SEQUENCE: 20

Xaa His Trp Ser Tyr Gly Leu Arg Pro Gly Ser Ser Gly Pro Ser Leu
1               5                   10                  15
Asp Glu Lys Lys Ile Ala Lys Met Glu Lys Ala Ser Ser Val Phe Asn
            20                  25                  30
Val Val Asn Ser Ser Ser Gly Pro Ser Leu His Trp Ser Tyr Gly Leu
        35                  40                  45
Arg Pro Xaa
    50
```

US 6,783,761 B2

CHIMERIC PEPTIDE IMMUNOGENS

This application claims priority from the provisional application No. 60/202,328, filed in the U.S. Patent and Trademark Office on May 5, 2000.

FIELD OF THE INVENTION

The invention is related to chimeric peptides having immunogenic efficacy, comprising a hormone epitope and promiscuous helper T-cell epitope for the production of high titers of anti-hormone antibodies.

BACKGROUND OF THE INVENTION

The success of an antigenic composition is linked to its immunogenicity, that is, the ability to produce a sufficiently high titer of antibodies to react or bind with the target antigen or so as to neutralize its effects. The immunogenicity depends on the effectiveness by which the antigen causes the body's immune system to mount a response which can be generally assessed on the basis of the antibody titer in the blood of the immunized animal or mammal including the human.

Antigenic formulations can be prepared for antigens of low immunogenicity with constructs or mixtures of an immunomimic epitope of the target antigen and an immunogen not related to the target antigen so as to generate a strong immune response against the entire immunogenic construct or mixture so as to be effective against the specific target antigen.

In order to enhance or potentiate the immune defense system, so-called adjuvants in the form of oily substances and other potentiating and emulsifying agents are added to the antigenic formulations. In general, the adjuvant is mixed into the immunogenic emulsion formulation and simultaneously delivered with the antigen in the same administration, e.g., by injection. Specifically, antigenic formulations have been enhanced to target less immunogenic microorganisms or viral pathogens by the addition of so-called adjuvants comprising immune response-stimulating killed microbial cells, particles or fragments thereof Moreover, immunogenic compositions may contain carrier components, including emulsions, liposomes, microparticles and implantable vehicles which may be metabolizable.

Immunization technology has been applied as a biological modifying means to immunize against various soluble and insoluble animal or human self-antigens, which are not normally recognized by the individual host's own immune defense, but which may be rendered immunogenic so as to stimulate or potentiate the individual's own immune response system. The self-antigens may include the surfaces of certain cells which are malfunctioning or malignant, and small proteins, enzymes or intercellular signals, such as, e.g., hormones or other factors, and/or their cognate receptors, whether normal or deficient. The lack of immunogenicity of these self-antigens has been often overcome by complexing or linking the non-immunogenic self-antigens with a pharmaceutically acceptable, i.e. non-toxic, immunogenic carrier so as to produce antibodies capable of binding, thereby neutralizing, the self-antigen of the subject animal or human patient.

The immunological methods can be used for example in the therapeutical hormone control or regulation and the treatment of patients afflicted with a disorder or disease.

Some immunogens suitable for hormone-regulation comprise hormone immunomimicking molecular moieties which are conjugated or fused to immunogenic carriers, such as, e.g., proteins, or peptides or complex polysugars. The immunogenic constructs are usually administered as either an oil-in-water or a water-in-oil emulsion, containing an adjuvant capable of stimulating or potentiating an immune response.

An immune response is typically measured in terms of the production of specific anti-hormone antibodies. The hormones and cognate receptors which are targeted for control by the immunological methods are directly neutralized or inhibited by the antigen-binding reaction of circulating hormone specific antibodies elicited by the injected immunogenic constructs.

For example, an anti-hormone immunogen has been constructed to affect the regulation of the gonadotropin releasing hormone (see co-assigned U.S. Pat. No. 5,688,506). The Gonadotropin Releasing Hormone (abbreviated "GnRH", also known as Luteinizing Hormone Releasing Hormone, abbreviated LHRH), is of central importance to the regulation of fertility. Johnson M et al., *Essential Reproduction*, 3$^{rd}$ Edn. Blackwell Scientific Publications (1988). In both males and females, GnRH is released from the hypothalamus into the bloodstream and is transported through the bloodstream to the pituitary, where it induces the release of gonadotropins, luteinizing hormone (LH) and follicle stimulating hormone (FSH), by the gonadotrophs. These gonadotropins, in turn, act upon the gonads, inducing steroidogenesis and gametogenesis. Steroids released from the gonads into the circulation subsequently act upon various tissues. This gonadotropin related hormonal cascade can be halted by the neutralization of the biological activity of GnRH. Fraser H. M., Physiological Effects of Antibody to Lutenizing Hormone Releasing Hormone, *Physiological Effects of Immunity Against Reproductive Hormones*, Edwards and Johnson, Eds. Cambridge University Press (1976). As a consequence of GnRH neutralization, the gonadotropins and gonadal steroids are not released into the blood, and their biological activities are curtailed or eliminated by the direct and indirect action of specific anti-GnRH antibodies. By eliminating the physiological activity of GnRH, the cascade of hormonal regulation of fertility is interrupted and gametogenesis ceases. Consequently, GnRH neutralization halts the production of gametes. Thus, GnRH neutralization is an effective means of contraception.

A number of important diseases are affected by gonadotropins and particularly gonadal steroid hormones. Such diseases include breast cancer, uterine and other gynecological cancers, endometriosis, uterine fibroids, benign prostatic hypertrophy and prostate cancer, among others. Removal of the gonadal steroid hormonal stimuli for these diseases constitutes an important means of therapy. An effective method of accomplishing this is by immunologically neutralizing GnRH, to thereby eliminate or inhibit production of GnRH dependent gonadal steroids that induce and stimulate these diseases. McLachlan R. I. et al. Clinical Aspects of LHRH Analogues in Gynaecology: a Review, *British Journal of Obstetrics and Gynaecology*, 93:431–454 (1986); Conn P. M. et al. Gonadotropin-Releasing Hormone and Its Analogs, *New England Journal of Medicine*. 324:93–103 (1991) and Filicori M. GnRH Agonists and Antagonists, Current Clinical Status. *Drugs*. 35:63–82 (1988).

Since GnRH has the same amino acid sequence in all mammals (pGlu-His-Trp-Ser-Tyr-Gly-Leu-Arg-Pro-GlyNH$_2$, SEQ ID NO: 1 in the Sequence Listing), it is presumed that a single immunogen would be effective in all mammalian species, including humans. An anti-GnRH immunogenic construct, comprising the GnRH immunomimic domain in the form of peptide analogues, may be linked or conjugated to a carrier protein which is effectively immunogenic, such as, e.g., diphtheria toxoid, tetanus toxoid, keyhole limpet hemocyanin, bovine serum albumin, pertussis extracts or filamentous Amycolata extracts. Consequently, the immune response to the GnRH-vaccine will be mostly directed against the carrier protein and secondarily, the attached hormone epitope moiety. In general, as an alternative approach, the immunogenicity of the immunomimic peptide can be enhanced by chemical modification with diazosulfuric acid groups.

Various anti-GnRH immunogenic compositions have been useful for producing specific anti-GnRH antibodies. Immunogenic conjugates of GnRH-immunomimic epitope peptide and immunogenic protein carriers have been used for immunization of vertebrate subjects against the hormone, GnRH (U.S. Pat. No. 5,688,506).

As another example, anti-hormone immunogens have been constructed to affect or inhibit the activity of the stomach hormone gastrin, in particular, the major forms of gastrin, gastrin G17 and gastrin G34 (see U.S. Pat. Nos. 5,023,077, and 5,468,494). It has been found that especially G17 is involved in gastrointestinal disorders and diseases such as gastroesophageal reflux disease, gastric and duodenal ulceration and cancer.

However, it has been found that perhaps due to the comparatively huge size of the attached immunogenic carrier proteins, the immunization of the conjugate can induce anti-epitope specific suppression of the antibody (Sad et al. Immunology, 1985, 74:559; Schutze et al. J. Immunol, 1985, 135:231). Therefore, much smaller immunogenic proteins have been tried. Accordingly, short synthetic T-helper epitopes have been introduced to replace the large carrier molecules in conjugates to improve the efficacy of the anti-hormone or self antigenic immunogen. Sad et al. (Vaccine 1993, 11:1145–1149) synthesized peptides from DT and universal or highly promiscuous T-helper epitopes from TT (829–844 amino acids, SEQ ID NO: 2) or CSP (378–398 aa; SEQ ID NO: 3) in order to try to minimize genetic restriction of the immune response. To be effective, the GnRH vaccines of Sad et al. required Freund's Complete Adjuvant.

Ghosh et al. (Int. *Immunology,* 1999, 11:1103–1110) reported that some synthetic LHRH (GnRH) chimeric vaccines elicited an immune response for sterilization of mice. However, the promiscuous helper T-cell ($T_h$)-epitope candidate T1 (TT sequence 947–967 aa, SEQ ID NO: 4) was not regarded promiscuous enough to be applicable for a large number of animal species. It was also reported that in a shift, antisera from second bleedings reacted significantly with the anti-$T_h$ epitope (T2) and much less with the LHRH antigen.

SUMMARY OF THE INVENTION

The present invention provides to immunogens comprising a chimeric peptide of a hormone-immunomimic peptide epitope fused in sequence with an immunogenic epitope. The hormone immunogenic peptide can be fused either directly to or through a spacer sequence to an immunogenic peptide epitope.

These fusion peptides combine at least one epitope of a target substance which may be non immunogen in its natural state with at least one immunogenic peptide sequence of suitable immunogenic proteins. The sequences of both target epitope and immunogen may be selected from the amino-terminal or carboxy-terminal region or both. A peptide also can be synthesized from the internal region of the peptide or protein. The fusion product may be acetylated at the amino-terminal end and amidated at the carboxy-terminal end of the peptide sequence.

An embodiment of the invention provides a synthetic immunogenic fusion peptide selected from the group consisting of one or more than one peptide defined by SEQ. ID NO: 10 and SEQ ID NO: 11.

BRIEF DESCRIPTION OF THE DRAWINGS

FIG. 1 illustrates the mean Anti-GnRH antibody titers obtained from rabbits using chimeric anti-GnRH Immunogens A through J, and as controls, Immunogens K and L as well as conjugate immunogen C GnRH:DT; and FIG. 2 illustrates the relationship between gross muscle reaction score and mean anti-GnRH Antibody Titer on GnRH Chimeras and Controls.

DETAILED DESCRIPTION OF THE INVENTION

Chimeric peptides comprising GnRH mimicking epitopes have been constructed and useful in generating improved antibody titers.

Since self-antigen epitopes of gonadotropin releasing hormone (GnRH) are not inherently immunogenic the immune response may be aided by immunogenic constructs according to the invention wherein a target peptide epitope is located on the same synthesized peptide as is an immunogenic peptide epitope.

Several different chimeric peptides are described in Example 1.

EXAMPLE I

The peptide sequences combine a select promiscuous T-helper-epitope through an inserted short spacer peptide (e.g., 4–8 amino acids) with at least one target hormone peptide. Suitable spacers of this invention include but are not limited to the peptides comprising the following amino acid sequence, GPSL (see SEQ ID NO: 5); SSGPSL (SEQ ID NO: 6); and SSGPSLKL (SEQ ID NO: 7), which are inserted in the peptide chimera to isolate the three dimensional folding of the immunogenic peptide from that of the hormone peptide.

Promiscuous Th-epitope moieties from measles virus protein F (MSF) (sequence 288–302 aa, SEQ ID NO: 8), tetanus toxoid (TT) (sequence 947–957 aa, SEQ ID NO: 4, or sequence 830–844 aa, SEQ ID NO: 2) and malaria Plasmodium falciparum CSP protein (sequence 378–398 aa, SEQ ID NO: 3) are used in these constructs. The hormone immunomimic epitopes were attached to the N-terminal or the C-terminus of the spacer as shown below. All mammalian GnRH peptides including the human hormone, have the same sequence. The GnRH hormone immunomimic epitope sequence comprises 1–10 amino acids of mammalian GnRH when attached to the aminoterminal peptide end and comprises 2–10 amino acids of mammalian GnRH when attached to the carboxyterminal peptide end. In addition, an immunomimic peptide comprising 13–16 amino acids of the mammalian GnRH comprise GnRH immunomimics peptides attached to both ends of the spacer, in order to increase the number of available GnRH antigenic epitopes. The different peptide chimera fusion immunogens in terms of antibodies produced are described below.

Peptide 1

→ Measles virus protein F sequence (288–302aa) →

| 1 | 2 | 3 | 4 | 5 | 6 | 7 | 8 | 9 | 10 | 11 | 12 | 13 | 14 | 15 |
|---|---|---|---|---|---|---|---|---|----|----|----|----|----|----|
| NH2—K | L | L | S | E | I | K | G | V | I | V | H | R | L | E |

←— spacer —→ ←— GnRH (2–10 aa) —→

| 16 | 17 | 18 | 19 | 20 | 21 | 22 | 23 | 24 | 25 | 26 | 27 | 28 | 29 | 30 |
|----|----|----|----|----|----|----|----|----|----|----|----|----|----|----|
| G | V | E | G | P | S | L | H | W | S | Y | G | L | R | P |

31
G—CONH2    (SEQ ID NO: 9 in the Sequence Listing).

Peptide 2

→ Tetanus toxoid sequence (947–967 aa) →

| 1 | 2 | 3 | 4 | 5 | 6 | 7 | 8 | 9 | 10 | 11 | 12 | 13 | 14 | 15 |
|---|---|---|---|---|---|---|---|---|----|----|----|----|----|----|
| NH2—F | N | N | F | T | V | S | F | W | L | R | V | P | K | V |

←— spacer —→ → GnRH (2–10 aa)

| 16 | 17 | 18 | 19 | 20 | 21 | 22 | 23 | 24 | 25 | 26 | 27 | 28 | 29 | 30 |
|----|----|----|----|----|----|----|----|----|----|----|----|----|----|----|
| S | A | S | H | L | E | G | P | S | L | H | W | S | Y | G |

31 32 33 34
L  R  P  G—CONH2

(SEQ ID NO: 10 in the Sequence Listing).

Peptide 3

→ Tetanus toxoid sequence (830–844 aa) →

| 1 | 2 | 3 | 4 | 5 | 6 | 7 | 8 | 9 | 10 | 11 | 12 | 13 | 14 | 15 |
|---|---|---|---|---|---|---|---|---|----|----|----|----|----|----|
| NH2—Q | Y | I | K | A | N | S | K | F | I | G | I | T | E | L |

←— spacer —→ → GnRH 2–10 aa

| 16 | 17 | 18 | 19 | 20 | 21 | 22 | 23 | 24 | 25 | 26 | 27 | 28 |
|----|----|----|----|----|----|----|----|----|----|----|----|----|
| G | P | S | L | H | W | S | Y | G | L | R | P | G—CONH2 |

(SEQ ID NO: 11 in the Sequence Listing)

Peptide 4

→ Malaria CSP Protein Sequence 378–398 aa →

| 1 | 2 | 3 | 4 | 5 | 6 | 7 | 8 | 9 | 10 | 11 | 12 | 13 | 14 | 15 |
|---|---|---|---|---|---|---|---|---|----|----|----|----|----|----|
| NH2—D | E | K | K | I | A | K | M | E | K | A | S | S | V | F |

←— spacer —→ → GnRH (sequence 2–10 aa)

| 16 | 17 | 18 | 19 | 20 | 21 | 22 | 23 | 24 | 25 | 26 | 27 | 28 | 29 | 30 |
|----|----|----|----|----|----|----|----|----|----|----|----|----|----|----|
| N | V | V | N | S | G | P | S | L | H | W | S | Y | G | L |

31 32 33
R  P  G—CONH2

(SEQ ID NO: 12 in the Sequence Listing).

Peptide 5

→ GnRH (sequence 1–10 aa) →   ←— spacer —→

| 1 | 2 | 3 | 4 | 5 | 6 | 7 | 8 | 9 | 10 | 11 | 12 | 13 | 14 | 15 |
|---|---|---|---|---|---|---|---|---|----|----|----|----|----|----|
| p-E | H | W | S | Y | G | L | R | P | G | S | S | G | P | S |

←— MVF-P (288–302 aa) →

| 16 | 17 | 18 | 19 | 20 | 21 | 22 | 23 | 24 | 25 | 26 | 27 | 28 | 29 | 30 |
|----|----|----|----|----|----|----|----|----|----|----|----|----|----|----|
| L | K | L | L | S | E | I | K | G | V | I | V | H | R | L |

31 32 33 46
E  G  V  E—COOH    (SEQ ID NO: 13 in the Sequence Listing).

Peptide 6

→ GnRH (sequence 1–10 aa) →   ←— spacer —→

| 1 | 2 | 3 | 4 | 5 | 6 | 7 | 8 | 9 | 10 | 11 | 12 | 13 | 14 | 15 |
|---|---|---|---|---|---|---|---|---|----|----|----|----|----|----|
| p-E | H | W | S | Y | G | L | R | P | G | S | S | G | P | S |

→ TT sequence 947–967 aa →

| 16 | 17 | 18 | 19 | 20 | 21 | 22 | 23 | 24 | 25 | 26 | 27 | 28 | 29 | 30 |
|----|----|----|----|----|----|----|----|----|----|----|----|----|----|----|
| L | F | N | N | F | T | V | S | F | W | L | R | V | P | K |

31 32 33 34 35 36 37
V  S  A  S  H  L  E—COOH (SEQ ID NO: 14 in the Sequence Listing).

Peptide 7

GnRH sequence 1–10 aa →   ←— spacer —→

| 1 | 2 | 3 | 4 | 5 | 6 | 7 | 8 | 9 | 10 | 11 | 12 | 13 | 14 | 15 |
|---|---|---|---|---|---|---|---|---|----|----|----|----|----|----|
| p-E | H | W | S | Y | G | L | R | P | G | S | S | G | P | S |

TT sequence 830–844 aa →

| 16 | 17 | 18 | 19 | 20 | 21 | 22 | 23 | 24 | 25 | 26 | 27 | 28 | 29 |
|----|----|----|----|----|----|----|----|----|----|----|----|----|----|
| L | Q | Y | I | K | A | N | S | K | F | I | G | I | T |

30 31
E  L—COOH    (SEQ ID NO: 15 in the Sequence Listing).

Peptide 8

GnRH sequence 1–10 aa →   ←— spacer —→

| 1 | 2 | 3 | 4 | 5 | 6 | 7 | 8 | 9 | 10 | 11 | 12 | 13 | 14 | 15 |
|---|---|---|---|---|---|---|---|---|----|----|----|----|----|----|
| p-E | H | W | S | Y | G | L | R | P | G | S | S | G | P | S |

←— M-CSP sequence 378–398 aa →

| 16 | 17 | 18 | 19 | 20 | 21 | 22 | 23 | 24 | 25 | 26 | 27 | 28 | 29 | 30 |
|----|----|----|----|----|----|----|----|----|----|----|----|----|----|----|
| L | D | E | K | K | I | A | K | M | E | K | A | S | S | V |

31 32 33 34 35 36
F  N  V  V  N  S—COOH (SEQ ID NO: 16 in the Sequence Listing).

Peptide 9

GnRH (sequence 1–10 aa) →   ←— spacer —→

| 1 | 2 | 3 | 4 | 5 | 6 | 7 | 8 | 9 | 10 | 11 | 12 | 13 | 14 | 15 |
|---|---|---|---|---|---|---|---|---|----|----|----|----|----|----|
| p-E | H | W | S | Y | G | L | R | P | G | S | S | G | P | S |

←— MVF-P (288–302 aa) →

| 16 | 17 | 18 | 19 | 20 | 21 | 22 | 23 | 24 | 25 | 26 | 27 | 28 | 29 | 30 |
|----|----|----|----|----|----|----|----|----|----|----|----|----|----|----|
| L | K | L | L | S | E | I | K | G | V | I | V | H | R | L |

←— spacer —→ → GnRH (2–10 aa)

| 31 | 32 | 33 | 34 | 35 | 36 | 37 | 38 | 39 | 40 | 41 | 42 | 43 | 44 | 45 | 46 |
|----|----|----|----|----|----|----|----|----|----|----|----|----|----|----|----|
| E | G | V | E | G | P | S | L | H | W | S | Y | G | L | R | P |

47
G—CONH2    (SEQ ID NO: 17 in the Sequence Listing).

Peptide 10

→ GnRH (sequence 1–10 aa) →   ←— spacer —→

| 1 | 2 | 3 | 4 | 5 | 6 | 7 | 8 | 9 | 10 | 11 | 12 | 13 | 14 | 15 |
|---|---|---|---|---|---|---|---|---|----|----|----|----|----|----|
| p-E | H | W | S | Y | G | L | R | P | G | S | S | G | P | S |

-continued

TT sequence 947–967 aa →

| 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|
| L | F | N | N | F | T | V | S | F | W | L | R | V | P | K |

← spacer → GnRH (2–10) →

| 31 | 32 | 33 | 34 | 35 | 36 | 37 | 38 | 39 | 40 | 41 | 42 | 43 | 44 | 45 | 46 |
|---|---|---|---|---|---|---|---|---|---|---|---|---|---|---|---|
| V | S | A | S | H | L | E | G | P | S | L | H | W | S | Y | G |

| 47 | 48 | 49 | 50 |
|---|---|---|---|
| L | R | P | G—CONH2 |

(SEQ ID NO: 18 in the Sequence Listing).

Peptide 11

| GnRH sequence 1–10 aa → ← spacer →

| 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|
| p-E | H | W | S | Y | G | L | R | P | G | S | S | G | P | S |

TT sequence 830–844 aa →

| 16 | 17 | 18 | 19 | 20 | 21 | 22 | 23 | 24 | 25 | 26 | 27 | 28 | 29 |
|---|---|---|---|---|---|---|---|---|---|---|---|---|---|
| L | Q | Y | I | K | A | N | S | K | F | I | G | I | T |

← spacer → → GnRH (2–10 aa) →

| 30 | 31 | 32 | 33 | 34 | 35 | 36 | 37 | 38 | 39 | 40 | 41 | 42 | 43 | 44 | 45 |
|---|---|---|---|---|---|---|---|---|---|---|---|---|---|---|---|
| E | L | S | S | G | P | S | L | H | W | S | Y | G | L | R | P |

| 46 |
|---|
| G—CONH2 |

(SEQ ID NO: 19 in the Sequence Listing).

Peptide 12

| GnRH sequence 1–10 aa → ← spacer →

| 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|
| p-E | H | W | S | Y | G | L | R | P | G | S | S | G | P | S |

← M-CSP sequence 378–398 aa →

| 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|
| L | D | E | K | K | I | A | K | M | E | K | A | S | S | V |

→ ← spacer → → GnRH (sequence 2–10 aa)

| 31 | 32 | 33 | 34 | 35 | 36 | 37 | 38 | 39 | 40 | 41 | 42 | 43 | 44 | 45 | 46 | 47 |
|---|---|---|---|---|---|---|---|---|---|---|---|---|---|---|---|---|
| F | N | V | V | N | S | S | S | G | P | S | L | H | W | S | Y | G |

| 48 | 49 | 50 | 51 |
|---|---|---|---|
| L | R | P | G—CONH2 |

(SEQ ID NO: 20 in the Sequence Listing).

EXAMPLE II

Immunogenicity tests were performed with five chimeric peptide immunogens against GnRH. Each chimeric peptide contained one region encoding an epitope to be recognized by helper T-cell and a second region encoding an immuno-mimic of GnRH, to serve as the target for the antibody response. The chimeric peptide immunogens were formulated to deliver 100, 250 or 500 µg doses of peptide with 3 µg norMDP, in a water in oil emulsion. Control immunogens were prepared to deliver 500 µg of mammalian GnRH (1–10) Ser1 peptide (which is normally linked to an immunogenic carrier to impart immunogenicity), with and without norMDP (3 µg), in the same emulsions. The immunogens were given intramuscularly to rabbits in three injections, on days 0, 14 and 42. An ELISA procedure was used to measure the resultant anti-GnRH antibody responses in sera collected at 14-day intervals over the course of the immunization. Injection site reactions were assessed by visual and microscopic evaluations on day 84.

The following materials were used in the immunogenicity tests. The five immunogens of GnRH chimera peptides tested were selected from the aforementioned Peptide 1 through 16.

1. GnRH chimera 1 {MVF (Measles Virus Protein F)} "Peptide 1" (MW 3427.17)
2. GnRH chimera 2 {TT-3 (Tetanus Toxoid Epitope 3)} "Peptide 2" (MW 3886.52)
3. GnRH chimera 3 {TT-2 (Tetanus Toxoid Epitope 2)} "Peptide 3" (MW 3132.6)
4. GnRH chimera 4 {MCSP (Malaria Circumsporozoite Protein)} "Peptide 4" (MW 3632.2)
5. GnRH chimera 6 (TT-3, N-ter GnRH) "Peptide 6" (MW 4172.7)
6. D17 Peptide ("GnRH (1–10) Ser 1")

For testing the GnRH chimeric peptide immunogens were formulated at concentrations listed below in Table 1. Each injection volume was 0.2 ml/dose (see Table 2).

TABLE 1

GnRH Chimera and Control Immunogen Formulations

| Immunogen | Chimeric Peptide | Concentration of Peptide in Emulsion (mg/ml) | Peptide Dose (µg/dose) | Concentration of norMDP in Emulsion (mg/ml) | norMDP Dose (µg/dose) |
|---|---|---|---|---|---|
| A | Peptide 1 | 2.5 | 500 | 0.015 | 3 |
| B | Peptide 2 | 2.5 | 500 | 0.015 | 3 |

TABLE 1-continued

GnRH Chimera and Control Immunogen Formulations

| Immunogen | Chimeric Peptide | Concentration of Peptide in Emulsion (mg/ml) | Peptide Dose (μg/dose) | Concentration of norMDP in Emulsion (mg/mi) | norMDP Dose (μg/dose) |
|---|---|---|---|---|---|
| C | Peptide 2 | 1.25 | 250 | 0.015 | 3 |
| D | Peptide 2 | 0.5 | 100 | 0.015 | 3 |
| E | Peptide 3 | 1.25 | 500 | $7.2 \times 10^{-3}$ | 3 |
| F | Peptide 4 | 2.5 | 500 | 0.015 | 3 |
| G | Peptide 6 | 2.5 | 500 | 0.015 | 3 |
| H | Peptide 2 | 2.5 | 500 | 0.015 | 3 |
| I | Peptide 3 | 1.25 | 500 | $7.2 \times 10^{-3}$ | 3 |
| J | Peptide 2 & 3 | 0.625, each peptide | 250, each peptide | $7.2 \times 10^{-3}$ | 3 |
| K | D17 Peptide | 2.5 | 500 | 0.015 | 3 |
| L | D17 peptide | 2.5 | 500 | — | — |

The GnRH chimeric immunogenic compositions and control immunogens were formulated under clean conditions in the combinations shown in Table 1. The test materials were sterile bottled and stored under refrigeration (2–8° C.).

New Zealand White female rabbits were immunized with GnRH chimera and control immunogens as shown in Table 2. Injections were given to each rabbit on days 0, 14 and 42 in dose volumes of either 0.2 ml or 0.4 ml. All immunogens were given IM, at injection sites tattooed for later identification.

To assess immunogenicity, sera were obtained from each rabbit every 14 days until day 84. Anti-GnRH antibody titers were measured in the sera samples by a direct binding ELISA. All values, with the exception of those for immunogen 6, are expressed relative to a reference standard rabbit anti-GnRH serum reference titer of 5,000. Titers of sera against Immunogen 6 (Peptide 6 N-terminal specific antibodies) were expressed relative to the reference standard rabbit anti-GnRH serum Ser 10(11) reference titer of 20,000. Although the original study had two rabbit groups, the protocol was later amended to add two more groups (n=4), 3 and 4, with amounts of 250 μg and 100 μg of GnRH chimera 2 (TT-3) (Peptide 2), each with 3 μg of norMDP.

TABLE 2

Example II: Immunization Schedule

| Rabbit Group Number | N* | Peptide(s) | Injection Volume (ml/dose) |
|---|---|---|---|
| 1 | 4 | Peptide 1 500 μg | 0.2 |
| 2 | 4 | Peptide 2 500 μg | 0.2 |
| 3 | 4 | Peptide 2 250 μg | 0.2 |
| 4 | 4 | Peptide 2 100 μg | 0.2 |
| 5 | 4 | Peptide 3 500 μg | (2 × 0.2/site)** |
| 6 | 4 | Peptide 4 500 μg | 0.2 |
| 7 | 4 | Peptide 6 500 μg | 0.2 |
| 8 | 10 | Peptide 2 500 μg | 0.2 |
| 9 | 10 | Peptide 3 500 μg | (2 × 0.2/site)** |
| 10 | 6 | Peptides 2 & 3, 250 μg each | (2 × 0.2/site)** |
| 11 | 4 | Dl7 peptide (500 μg) with norMDP | 0.2 |
| 12 | 4 | Dl7 peptide 500 μg | 0.2 |

*N = number of rabbits per group
**Peptide 3 did not dissolve at higher concentrations, therefore injection volumes were doubled to deliver 500 μg/dose of total peptide.

Since GnHR chimera peptide 3 ("Peptide 3") (TT-2) was not found soluble at 9.412 mg/ml in aqueous phase, the original protocol was amended to reduce the concentration in half (4.706 mg/ml) and double the dose volume to maintain 0.2 ml volume per injection (2×0.2 ml/site). Injection #3 was delivered on day 42.

Titers obtained for the individual serum samples are given in Table 3A/B/C, and mean titers for all groups are plotted in FIG. 1, respectively. In the initial tests, all rabbits responded to the chimera peptides with the production of anti-GnRH antibody titers. Peptide 3 or GnRH chimera 3 (TT-2) induced significantly higher antibody titers in comparison with the other chimera peptides. Peptide 2 or Chimera 2 was most immunogenic at the 500 μg dose (Immunogen B), with the 100 μg (Immunogen D) and 250 μg (Immunogen C) doses inducing weaker titers. Chimeras 2 (Immunogen B) and 3 (Immunogen E) induced high antibody titers in the initial tests (n=4) relative to titers induced by GnRH:DT; however, these titers were lower in the repeat studies (n=10, Immunogen H where the response rate was quite variable, and Immunogen I, respectively).

Figure 2:
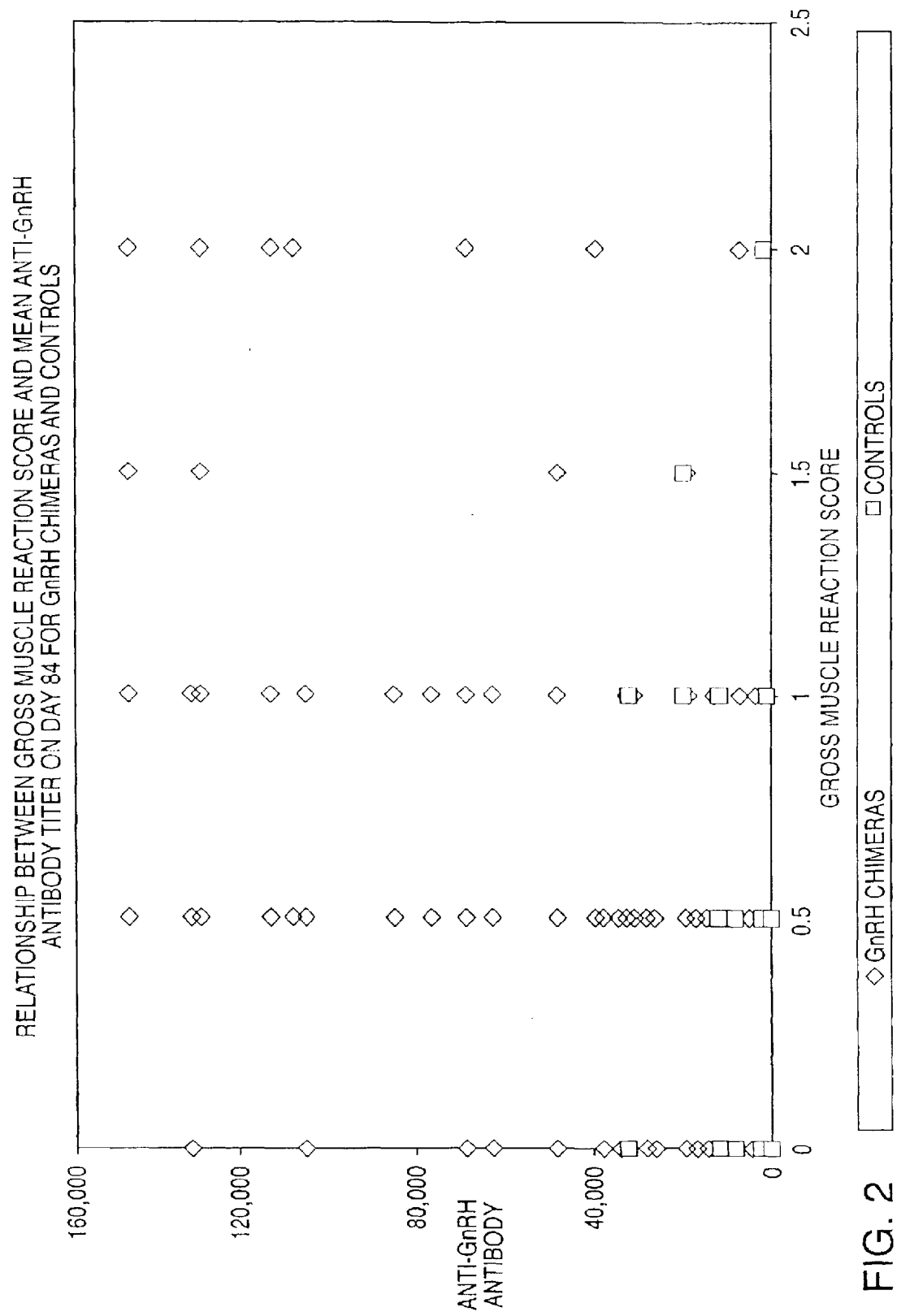

A combination of Chimeras 2 and 3 (Immunogen J), at 250 μg dose of each (half the dose used in rabbits injected with the individual peptides) induced high titers of anti-GnRH antibody. Chimeras 1 (Immunogen A), 4 (Immunogen F) and 6 (Immunogen G) were not as potent as the GnRH:DT conjugate formulated in Montanide ISA 703 (as historical control included in FIGS. 1 and 2). It should be noted that Peptide 6 or GnRH chimera 6 (TT-3 in amino-terminal position) titers were measured using an N-terminus specific reference standard, therefore a statistical comparison of these titers with other chimera peptides was not performed. Nevertheless, Peptide 6 was concluded not to be an effective immunogen. Very low anti-GnRH antibody titers were induced by D17 peptide adjuvanted with norMDP (Immunogen K), while without norMDP (Immunogen L), the D17 peptide emulsion was not immunogenic.

Gross pathology of injection sites was assessed on all rabbits on day 84. The evaluation was scored on a scale of 0–3, where a score of 0 indicated normal tissue appearance and 3 indicated the presence of extensive tissue inflammation. Scores of 1 or 2 were judged intermediate levels of local reaction.

TABLE 3A

Example II: Anti-GnRH Antibody Titers for GnRH Chimeras

| Immunogen | Rabbit # | Injection 1 (Day 0) Day 0 | Injection 2 (Day 14) Day 14 | Day 28 | Injection 3 (Day 42) Day 42 | Day 56 | Day 70 | Day 84 |
|---|---|---|---|---|---|---|---|---|
| A | 1 | 0 | 274 | 3,276 | 8,845 | 12,500 | 20,600 | 13,200 |
|  | 2 | 0 | 0 | 636 | 2,193 | 4,667 | 13,400 | 8,249 |
|  | 3 | 0 | 0 | 198 | 512 | 731 | 1,392 | 1,166 |
|  | 4 | 0 | 0 | 0 | 0 | 0 | 0 | 0 |
|  | Mean | 0 | 69 | 1,028 | 2,888 | 4,475 | 8,848 | 5,654 |
|  | Median | 0 | 0 | 417 | 1,353 | 2,699 | 7,396 | 4,708 |
|  | S.D. | 0 | 137 | 1,522 | 4,081 | 5,729 | 9,878 | 6,213 |
| B | 5 | 0 | 8,201 | 20,500 | 37,400 | 34,500 | 62,100 | 76,800 |
|  | 6 | 0 | 12,400 | 46,400 | 81,200 | 134,000 | 93,100 | 108,000 |
|  | 7 | 0 | 507 | 22,300 | 91,800 | 75,000 | 50,600 | 28,400 |
|  | 8 | 0 | 589 | 2,085 | 16,100 | 24,800 | 31,800 | 32,700 |
|  | Mean | 0 | 5,424 | 22,821 | 56,625 | 67,075 | 59,400 | 61,475 |
|  | Median | 0 | 4,395 | 21,400 | 59,300 | 54,750 | 56,350 | 54,750 |
|  | S.D. | 0 | 5,886 | 18,181 | 35,838 | 49,632 | 25,705 | 37,953 |
| C | 9 | 0 | 0 | 536 | 1,325 | 6,631 | 7,267 | 5,033 |
|  | 10 | 0 | 0 | 1,240 | 3,551 | 19,700 | 19,600 | 7,886 |
|  | 11 | 0 | 0 | 719 | 16,800 | 12,800 | 16,800 | 11,200 |
|  | 12 | 0 | 0 | 454 | 2,671 | 5,017 | 5,844 | 3,692 |
|  | Mean | 0 | 0 | 737 | 6,087 | 11,037 | 12,378 | 6,953 |
|  | Median | 0 | 0 | 628 | 3,111 | 9,716 | 12,034 | 6,460 |
|  | S.D. | 0 | 0 | 353 | 7,201 | 6,679 | 6,844 | 3,328 |
| D | 13 | 0 | 2,952 | 8,320 | 869 | 87,200 | 47,300 | 39,700 |
|  | 14 | 0 | 841 | 21,600 | 57,500 | 93,000 | 25,100 | 11,800 |
|  | 15 | 0 | 141 | 1,759 | 4,373 | 7,732 | 6,670 | 5,198 |
|  | 16 | 0 | 0 | 5,220 | 7,044 | 7,363 | 6,120 | 4,731 |
|  | Mean | 0 | 984 | 9,225 | 17,447 | 48,824 | 21,298 | 15,357 |
|  | Median | 0 | 491 | 6,770 | 5,709 | 47,466 | 15,885 | 8,499 |
|  | S.D. | 0 | 1,363 | 8,674 | 26,822 | 47,721 | 19,450 | 16,546 |
| E | 17 | 0 | 1,382 | 15,500 | 140,000 | 79,900 | 136,000 | 105,000 |
|  | 18 | 0 | 264 | 13,200 | 50,800 | 41,700 | 120,000 | 145,000 |
|  | 19 | 0 | 471 | 13,000 | 98,900 | 95,700 | 111,000 | 131,000 |
|  | 20 | 0 | 2,317 | 13,400 | 35,900 | 52,800 | 80,500 | 85,100 |
|  | Mean | 0 | 1,109 | 13,775 | 81,400 | 67,525 | 111,875 | 116,525 |
|  | Median | 0 | 927 | 13,300 | 74,850 | 66,350 | 115,500 | 118,000 |
|  | S.D. | 0 | 941 | 1,162 | 47,423 | 24,703 | 23,332 | 26,713 |
| F | 21 | 0 | 296 | 3,189 | 2,638 | 2,165 | 2,751 | 3,365 |
|  | 22 | 0 | 0 | 441 | 5,920 | 4,912 | 8,760 | 12,200 |
|  | 23 | 0 | 0 | 484 | 6,350 | 6,333 | 7,900 | 7,512 |
|  | 24 | 0 | 0 | 3,556 | 60,300 | 20,400 | 24,300 | 18,700 |
|  | Mean | 0 | 74 | 1,918 | 18,802 | 8,453 | 10,928 | 10,444 |
|  | Median | 0 | 0 | 1,837 | 6,135 | 5,623 | 8,330 | 9,856 |
|  | S.D. | 0 | 148 | 1,687 | 27,716 | 8,151 | 9,301 | 6,582 |

TABLE 3B

Example II: Anit-GnRH Antibody Titers for GnRH Chimeras continued)

| Immunogen | Rabbit # | Injection 1 (Day 0) Day 0 | Injection 2 (Day 14) Day 14 | Day 28 | Injection 3 (Day 42) Day 42 | Day 56 | Day 70 | Day 84 |
|---|---|---|---|---|---|---|---|---|
| G | 25 | 0 | 0 | 0 | 0 | 105 | 640 | 1,165 |
|  | 26 | 0 | 0 | 0 | 0 | 0 | 131 | 141 |
|  | 27 | 0 | 0 | 0 | 166 | 914 | 3,554 | 3,830 |
|  | 28 | 0 | 0 | 0 | 191 | 387 | 1,265 | 1,510 |
|  | Mean | 0 | 0 | 0 | 89 | 352 | 1,398 | 1,662 |
|  | Median | 0 | 0 | 0 | 83 | 246 | 953 | 1,338 |
|  | S.D. | 0 | 0 | 0 | 104 | 409 | 1,511 | 1,558 |
| H | 29 | 0 | 0 | 0 | 0 | 208 | 708 | 693 |
|  | 30 | 0 | 0 | 1,257 | 1,475 | 2,800 | 2,374 | 2,313 |
|  | 31 | 0 | 0 | 0 | 0 | 0 | 0 | 0 |
|  | 32 | 0 | 0 | 0 | 147 | 1,319 | 2,051 | 1,559 |
|  | 33 | 0 | 204 | 3,713 | 8,696 | 11,900 | 14,100 | 11,200 |
|  | 34 | 0 | 0 | 413 | 480 | ** | 16,900 | 14,700 |
|  | 35 | 0 | 0 | 366 | 326 | 1,879 | 3,462 | 3,022 |
|  | 36 | 0 | 0 | 0 | 0 | 200 | 410 | 555 |
|  | 37 | 0 | 0 | 163 | 774 | 2,825 | 4,677 | 5,109 |
|  | 38 | 0 | 2,787 | 8,027 | 7,742 | 41,700 | 63,200 | 62,900 |

TABLE 3B-continued

Example II: Anit-GnRH Antibody Titers for GnRH Chimeras continued)

| Immunogen | Injection→<br>Rabbit # | Injection 1<br>(Day 0)<br>Day<br>0 | Injection 2<br>(Day 14)<br>Day<br>14 | Day<br>28 | Injection 3<br>(Day 42)<br>Day<br>42 | Day<br>56 | Day<br>70 | Day<br>84 |
|---|---|---|---|---|---|---|---|---|
| | Mean | 0 | 299 | 1,394 | 1,964 | 6,981 | 10,788 | 10,205 |
| | Median | 0 | 0 | 265 | 403 | 1,879 | 2,918 | 2,668 |
| | S.D. | 0 | 877 | 2,597 | 3,335 | 13,523 | 19,319 | 19,149 |
| I | 39 | 0 | 0 | 228 | 877 | 7,841 | 12,200 | 9,998 |
| | 40 | 0 | 0 | 2,568 | 5,522 | 27,000 | 29,600 | 17,000 |
| | 41 | 0 | 895 | 7,474 | 31,400 | 29,500 | 46,300 | 34,500 |
| | 42 | 0 | 0 | 1,560 | 3,280 | 10,800 | 12,000 | 11,500 |
| | 43 | 0 | 222 | 3,510 | 16,600 | 20,600 | 31,300 | 26,500 |
| | 44 | 0 | 0 | 5,825 | 22,500 | 27,000 | 36,200 | 37,900 |
| | 45 | 0 | 1,249 | 24,300 | 39,300 | 65,000 | 67,700 | 69,100 |
| | 46 | 0 | 498 | 5,208 | 7,243 | 8,877 | 13,500 | 16,800 |
| | 47 | 0 | 0 | 2,091 | 5,509 | 10,100 | 19,200 | 18,300 |
| | 48 | 0 | 0 | 4,072 | 7,937 | 14,600 | 26,300 | 46,400 |
| | Mean | 0 | 286 | 5,684 | 14,017 | 22,132 | 29,430 | 29,000 |
| | Median | 0 | 0 | 3,791 | 7,590 | 17,600 | 27,950 | 22,400 |
| | S.D. | 0 | 452 | 6,886 | 13,061 | 17,164 | 17,535 | 18,782 |
| J | 49 | 0 | 219 | 4,179 | 33,900 | 81,500 | 85,300 | 113,000 |
| | 50 | 0 | 8,659 | 100,00 | 193,000 | 242,000 | 169,000 | 129,000 |
| | 51 | 0 | 305 | 0 | 89,500 | 91,300 | 97,800 | 69,000 |
| | 52 | 0 | 1,071 | 14,800 | 26,600 | 30,600 | 27,500 | 19,300 |
| | 53 | 0 | 554 | 11,000 | 64,000 | 32,500 | 31,400 | 31,100 |
| | 54 | 0 | 1,940 | 16,300<br>32,700 | 86,400 | 70,500 | 65,600 | 68,800 |
| | Mean | 0 | 2,125 | 29,830 | 82,333 | 91,400 | 79,433 | 71,700 |
| | Median | 0 | 813 | 15,550 | 75,200 | 76,000 | 75,450 | 68,900 |
| | S.D. | 0 | 3,263 | 35,647 | 60,172 | 77,950 | 52,134 | 43,356 |
| K | C1 | 0 | 746 | 1,515 | 2,201 | 1,918 | 2,074 | 1,913 |
| | C2 | 0 | 0 | 0 | 0 | 0 | 0 | 0 |
| | C3 | 0 | 134 | 590 | 953 | 998 | 1,238 | 1,768 |
| | C4 | 0 | 323 | 2,279 | 1,345 | 1,225 | 1,640 | 987 |
| | Mean | 0 | 301 | 1,096 | 1,125 | 1,035 | 1,238 | 1,167 |
| | Median | 0 | 229 | 1,053 | 1,149 | 1,112 | 1,439 | 1,378 |
| | S.D. | 0 | 325 | 1,005 | 913 | 793 | 893 | 878 |
| L | C5 | 0 | 0 | 0 | 0 | 0 | 0 | 0 |
| | C6 | 0 | 0 | 0 | 0 | 0 | 0 | 0 |
| | C7 | 0 | 0 | 0 | 0 | 107 | 0 | 0 |
| | C8 | 0 | 0 | 0 | 0 | 0 | 0 | 0 |
| | Mean | 0 | 0 | 0 | 0 | 27 | 0 | 0 |
| | Median | 0 | 0 | 0 | 0 | 0 | 0 | 0 |
| | S.D. | 0 | 0 | 0 | 0 | 54 | 0 | 0 |

TABLE 3C

Example II: Anit-GnRH Antibody Titers for GnRH Chimeras

| Immunogen | Injection→<br>Rabbit # | Injection 1<br>(Day 0)<br>Day<br>0 | Injection 2<br>(Day 14)<br>Day<br>14 | Day<br>28 | Injection 3<br>(Day 42)<br>Day<br>42 | Day<br>56 | Day<br>70 | Day<br>84 |
|---|---|---|---|---|---|---|---|---|
| Control | C9 | 0 | 475 | 7,210 | 11,400 | 8,812 | 8,762 | 8,338 |
| GnRHDT Conjugate in | C10 | 0 | 1,588 | 9,253 | 20,100 | 28,500 | 34,800 | 32,200 |
| Emulsion = 0.5 mg/ml | C11 | 0 | 0 | 4,593 | 17,700 | 25,100 | 35,400 | 19,800 |
| Conjugate Dose = 100 µg | C12 | 0 | 194 | 3,647 | 7,900 | 13,900 | 12,900 | 11,800 |
| Dose Volume = 0.2 ml | C13 | 0 | 169 | 1,565 | 2,559 | 4,752 | 7,204 | 7,115 |
| | C14 | 0 | 651 | 3,965 | 3,755 | 8,277 | 13,700 | 7,179 |
| | C15 | 0 | 123 | 2,785 | 2,627 | 4,198 | 5,218 | 3,891 |
| | C16 | 0 | 353 | 4,910 | 13,800 | 26,700 | 43,600 | 30,600 |
| | C17 | 0 | 333 | 8,573 | 25,100 | 30,300 | 57,400 | 26,200 |
| | C18 | 0 | 188 | 2,171 | 2,622 | 7,314 | 8,207 | 8,404 |
| | Mean, Group 5 | 0 | 407 | 4,867 | 10,756 | 15,785 | 22,719 | 15,553 |
| | Median, Group 5 | 0 | 264 | 4,279 | 9,650 | 11,356 | 13,300 | 10,102 |
| | S.D. | 0 | 455 | 2,653 | 8,216 | 10,617 | 18,486 | 10,695 |

* test titers are read at 20,000 titer of the reference standard, lot 122298SHG2

The score data are summarized in Table 4, indicating that most of the visual injection site scores ranged from 0 to 1, indicating that the immunogens were generally well tolerated.

Histologic readings of the injection site biopsies which were performed as of day 84 were in accord with the gross evaluation.

These experiments demonstrated that chimera peptides carrying a T-lymphocyte epitope and expressing an immunomimic of GnRH can be used to induce potent anti-GnRH antibody responses. Peptides bearing TT-2 and TT-3 T-lymphocyte epitopes, derived from TT, were more effective than the T-lymphocyte epitopes derived from MVF and MCSP. A combination of the TT-2 and TT-3 bearing chimeras was particularly effective. It was surprisingly found that the GnRH epitope had to be on the carboxyterminus of the chimeras to be immunogenic. Most injection site reactions were of an acceptable level. Overall, the response compared favorably with those induced by the GnRH:DT (previously named, D17-DT) conjugate, indicating that the synthetic peptides could potentially enhance the choice of effective immunogens and perhaps even replace the conjugate method for producing an active component of the GnRH immunogen.

TABLE 4

Example II: Reaction Scores

| | MEAN REACTION SCORES | | | | | | REACTION SCORES >1 | | | | | |
|---|---|---|---|---|---|---|---|---|---|---|---|---|
| | Injection 1 | | Injection 2 | | Injection 3 | | Injection 1 | | Injection 2 | | Injection 3 | |
| Immunogen | SITE 1 | SITE 2 | SITE 1 | SITE 2 | SITE 1 | SITE 2 | SITE 1 | SITE 2 | SITE 1 | SITE 2 | SITE 1 | SITE 2 |
| A | 0 | | 0.5 | | 0.5 | | 0 | | 0 | | 0 | |
| B | 0.4 | | 1.1 | | 1.1 | | 0 | | 1 | | 1 | |
| C | 0.1 | | 0.5 | | 0.5 | | 0 | | 0 | | 0 | |
| D | 0.3 | | 0.4 | | 1.0 | | 0 | | 0 | | 1 | |
| E | 0.6 | 0.3 | 0.9 | 0.6 | 0.8 | 1.3 | 0 | 0 | 1 | 0 | 0 | 1 |
| F | 0.5 | | 1.1 | | 1.1 | | 0 | | 1 | | 1 | |
| G | 0.1 | | 0.3 | | 0.8 | | 0 | | 0 | | 0 | |
| H | 0.1 | | 0.3 | | 0.4 | | 0 | | 0 | | 0 | |
| I | 0 | 0.4 | 0.1 | 0.5 | 0.6 | 0.7 | 0 | 0 | 0 | 0 | 1 | 1 |
| J | 0 | 0.4 | 0.5 | 0.5 | 1.0 | 1.3 | 0 | 0 | 0 | 0 | 1 | 2 |
| K | 0.4 | | 0.4 | | 1.0 | | 0 | | 0 | | 1 | |
| L | 0.3 | | 0 | | 0.3 | | 0 | | 0 | | 0 | |
| Conjugate Ctl. | 0.4 | | 0.6 | | 0.9 | | 0 | | 0 | | 1 | |

What is claimed is:

1. A synthetic immunogen for inducing specific antibodies against GnRH comprising:
   (i) a promiscuous helper T-lymphocyte epitope selected from the group consisting of SEQ ID NO: 8 of measles virus protein F (MVP-F), SEQ ID NO: 2, SEQ ID NO: 4 of tetanus toxoid (TT), and SEQ ID NO: 3 of malaria circumsporozoite protein (M-CSP), fused through
   (ii) a spacer peptide selected from the group consisting of Gly-Pro-Ser-Leu (SEQ ID NO: 5), Ser-Ser-Gly-Pro-Ser-Leu (SEQ ID NO: 6), and Ser-Ser-Gly-Pro-Ser-Leu-Lys-Leu (SEQ ID NO: 7) to
   (iii) a GnRH immunonmimic peptide comprising either the amino acid sequence of SEQ ID NO: 1, or amino acids 2–10 of SEQ ID NO: 1.

2. The synthetic immunogen of claim 1, wherein the T-lymphocyte epitope is fused through the spacer peptide to the amino-terminus or the carboxy-terminus of the GnRH-immunomimic peptide.

3. The synthetic immunogen of claim 2, further comprising a second GnRH immunomimic peptide comprising either the amino acid sequence of SEQ ID NO: 1 or amino acids 2–10 of SEQ ID NO: 1 wherein the second GnRH immunomimic peptide is fused at its carboxy-terminus or its amino-terminus through a spacer peptide to the T-lymphocyte epitope.

4. The synthetic immunogen of claim 1 wherein the T-lymphocyte epitope is fused through a spacer peptide to the amino-terminus of the GnRH-immunomimic is peptide.

5. The synthetic immunogen of claim 1 comprising a GnRH-immunomimic peptide having an acetylated amino terminal glutamic acid or an amidated carboxy-terminal glycine.

6. A synthetic immunogen for inducing specific antibodies against GnRH comprising a promiscuous helper T-lymphocyte epitope fused through a spacer peptide to a GnRH immunomimic peptide selected from the group consisting of the peptide defined by SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, or SEQ ID NO; 20.

7. The synthetic immunogen of claim 6, wherein the synthetic immunogen is the peptide defined by SEQ ID NO: 10 or SEQ ID NO: 11.

8. A combination of synthetic immunogens for inducing specific antibodies against GnRH comprising at least two different synthetic immunogens selected from the group consisting of the peptide defined by SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO. 17, SEQ ID NO: 18, SEQ ID NO: 19, or SEQ ID NO: 20.

9. The combination of synthetic immunogens according to claim 8, comprising:
   (i) the synthetic immunogen defined by SEQ ID NO: 10; and
   (ii) the synthetic immunogen defined by SEQ ID NO: 11.

10. An injectable pharmaceutical composition comprising the synthetic immunogen of claim 1, and a pharmaceutically acceptable carrier.

11. The injectable pharmaceutical composition of claim 10, comprising a synthetic immunogen selected from the group consisting of the peptide defined by SEQ ID NO: 9, SEQ ID NO; 10, SEQ ID NO: 11, SEQ ID NO: 12, SEQ ID NO: 13, SEQ ID NO; 14, SEQ ID NO: 15, SEQ ID NO: 16, SEQ ID NO: 17, SEQ ID NO: 18, SEQ ID NO: 19, or SEQ ID NO: 20; and a pharmaceutically acceptable carrier.

12. The injectable pharmaceutical composition of claim 11, comprising the synthetic immunogen defined by SEQ ID NO: 10 or SEQ ID NO: 11; and a pharmaceutically acceptable carrier.

13. An injectable pharmaceutical composition comprising the combination of synthetic immunogens of claim 8, and a pharmaceutically acceptable carrier.

14. The injectable pharmaceutical composition of claim 13, comprising:
   (i) the synthetic immunogen defined by SEQ ID NO: 10;
   (ii) the synthetic immunogen defined by SEQ ID NO: 11; and
   (iii) a pharmaceutically acceptable carrier.

* * * * *

UNITED STATES PATENT AND TRADEMARK OFFICE
CERTIFICATE OF CORRECTION

PATENT NO. : 6,783,761 B2
DATED : August 31, 2004
INVENTOR(S) : Grimes et al.

It is certified that error appears in the above-identified patent and that said Letters Patent is hereby corrected as shown below:

Column 31,
Line 21, "circumsporozoitc," should read -- circumsporozoite --.
Line 26, "immunonmimic" should read -- immunomimic --.
Line 30, "T-lymphocytc" should read -- T-lymphocyte --.
Line 43, "immunomimic is peptide" should read -- immunomimic peptide --.
Lines 45-46, "amino terminal" should read -- amino-terminal --.
Lines 54-55, "SEQ ID NO; 20" should read -- SEQ ID NO: 20 --.

Column 32,
Line 38, "SEQ ID NO; 14" should read -- SEQ ID NO: 14 --.

Signed and Sealed this

Thirtieth Day of November, 2004

JON W. DUDAS
*Director of the United States Patent and Trademark Office*